United States Patent [19]
Witten et al.

[11] Patent Number: 5,998,376
[45] Date of Patent: Dec. 7, 1999

[54] SUBSTANCE P TREATMENT FOR IMMUNOSTIMULATION

[76] Inventors: Mark L. Witten, 7032 E. Rosewood St., Tuson, Ariz. 85710; David T. Harris, 4100 N. Alvernon Way, Tucson, Ariz. 85718

[21] Appl. No.: 09/028,003

[22] Filed: Feb. 23, 1998

Related U.S. Application Data

[62] Division of application No. 08/829,445, Mar. 28, 1997
[60] Provisional application No. 60/022,063, Jul. 23, 1996.

[51] Int. Cl.$^6$ .......................... A61K 38/02; A61K 38/08; C07K 7/06
[52] U.S. Cl. ...................... 514/15; 514/2; 930/DIG. 802; 424/278.1
[58] Field of Search ........................ 514/2, 15; 424/278.1

[56] References Cited

U.S. PATENT DOCUMENTS

| | | | |
|---|---|---|---|
| 5,314,690 | 5/1994 | Patterson et al. | 424/88 |
| 5,410,019 | 4/1995 | Coy et al. | 530/323 |

FOREIGN PATENT DOCUMENTS 0 545 478 A1   6/1993   European Pat. Off. .

OTHER PUBLICATIONS

Lotz et al., "B Cell Stimulating Factor 2/Interleukin 6 is a Costimulant for Human Thymocytes and T Lymphocytes", *J. Exp. Med.*, 167:1253–1258 (1988).
Tammy Kincy–Cain et al., "Substance P–Induced IL–12 Production by Murine Macrophages", The American Association of Immunologists, 158(5):2334–2339 (1997).
Xiao–Ying Yu, "Protective effect of substance P on permeability of airway epithelial cells in culture", American Physiological Society 889–895, (1996).
Garman et al., "B–Cell–Stimulatory Factor 2 ($\beta_2$ Interferon) Functions as a Second Ssignal for Interleukin 2 Production bvy Mature Murine T Cells", *Proc. Natl. Acad. Sci. USA* 84:7629–7633 (1987).
Pfaff et al., "Inhalation Exposure to JP–8 Jet Fuel Alters Pulmonary Function and Substance P Levels in Fischer 344 Rats", *J. Appl. Toxicol* 15(4):249–256 (1995).
Lotz et al., "Effect of Neuropeptides on Production of Inflammatory Cytokines by Human Monocytes", *Science* 241:1218–1221 (1988).
Kincy–Cain et al., Increased Susceptibility of Mice to Salmonella Infection Following In Vivo Treatment with the Substance P Antagonist, Spantide II, *The Journal of Immunology*, 157:255–264, 1996.
Palermo et al., "Bronchospasm Induced by Inhalation of Substance P: Effect of Sodium Cromoglycate", *Respiration* 54:95–99 (1988).
Boichot et al., "Inhaled Substance P Induces Actgivation of Alveolar Macrophages and Increases Airway Responses in the Guinea–Pig", *Neorpeptides* 25(307–313) (1993).
Pfaff et al., "Neutral Endopeptidase (NEP) and its Role in Pathological Pulmonary Change with Inhalation Exposure to JP–8 Jet Fuel", *Toxicology and Industrial Health* 12(1):93–103 (1996).
Jurjus A, Walsh R, "Detection of substance P positive cells and nerve fibers in the rat thymus," *The Faseb Journal*, 11(3):A201, 1997.
Hays et al., "Changes in Lung Permeability Correlate with Lung Histology in a Chronic Exposure Model", *Toxicology and Industrial Health* 11(3):325–336 (1995).
Kudlacz E. J. Neuroimmunology, 50, 119–125, Jan. 1994.
Siemion I.Z. et al. Molecular Immunology, 27, 887–890, Sep. 1990.

*Primary Examiner*—Cecilia J. Tsang
*Assistant Examiner*—Michael Borin
*Attorney, Agent, or Firm*—Banner & Witcoff, Ltd.

[57] ABSTRACT

Substance P aerosols are effective in replenishing immune systems compromised by environmental toxicants. They are also useful for prophylaxis against and treatment of infections and neoplasms. They are useful for accelerating maturation of immune systems or maintaining immune function, as well. Chronic exposure to hydrocarbons is particularly damaging to the immune system, and thus this occupational hazard can be counteracted by treatment with substance P aerosols.

7 Claims, 5 Drawing Sheets

SUBSTANCE P TREATMENT FOR IMMUNOSTIMULATION

This application is a divisional application of Ser. No. 08/829,445, filed Mar. 28, 1997, and claims the benefit of provisional application 60/022,063, filed Jul. 23, 1996.

The U.S. Government has a paid-up license in this invention and the right in limited circumstances to require the patent owner to license others on reasonable terms as provided for by the terms of Air Force Office of Scientific Research grant F49620-94-1-0297.

BACKGROUND OF THE INVENTION

Substance P belongs to a family of bioactive neuropeptides known as the tachykinins. Payan (1989) *Ann. Rev. Med.* 40:341. It is believed to be involved in the neurotransmission of pain sensation as well as a host of other biological functions.

Chronic exposure to jet fuel, common among refueling crews and aircraft mechanics, causes a wide variety of symptoms. Workers in a jet motor factory, for example, reported headaches, dizziness, and "thoracic oppression" (Struwe et al., *Acta Psychiat. Scand.* 303(S):55–67 (1983); Dossing et al., *Scand. J. Work Environ. Health* 11:433–437 (1985)). Inhaled and absorbed hydrocarbons or their metabolites may act on the central nervous system to produce neurasthenic syndrome in subjects exposed to jet fuel (Struwe et al, 1983, supra). Jet fuel may also have toxic effect on the liver, kidneys, and pulmonary system (Struwe et al., 1983 supra; Gaworski, et aL, (1984) in: Advances in Modern Environmental Toxicology, Vol. VI, Applied Toxicology of Petroleum Hydrocarbons (H. N. MacFarland, C. E. Holdsworth, J. A. MacGregor, R. W. Call, and M. L. Kane, eds.), Princeton Scientific Publishers, Princeton, N.J. pp. 33–47; Dossing et al., 1985, supra; Witten et al., (1990), Substance P and Related Peptides: Cellular and Molecular Physiology International Symposium, University of Massachusetts Press and the New York Academy of Science, p. 29.; Matie et al., *Toxicol Pathol.* 19(2):77–87 (1991)). Occupational exposure to jet fuel causes mucous membrane irritation, enhancing the clearance of antipyrine. The antipyrine test assesses microsomal enzyme activity, which can be altered by organic solvents (Dossing et al., 1985, supra).

JP-8 jet fuel is a kerosene type fuel which has become the United States military's main fuel source for aircraft as well as other types of military equipment. However, as discussed above, there are indications that jet fuel inflicts damage on those who must work with it.

Exposure to environmental toxicants may have significant effects on host systems beyond those readily visible (e.g., physiology, cardiology, respiratory, etc.) Such exposure may have profound and detrimental effects on the immune system that result in significant host impairment in terms of immune competence, susceptibility to infections, and future development of neoplasms.

Depending on the type of environmental toxicant and the route of exposure, the damage to the immune system may be minor and inconsequential, or it may be deleterious with long-lasting effects. Significant changes in immune competence, even if short-lived, may have serious consequences for the exposed host in terms of lymphopenia that may impinge upon susceptibility to infectious agents. Major alterations in immune function that are long-lasting may result in increased likelihood of development of cancer and autoimmune disease.

Viral infections, such as HIV, can also impinge upon the welfare of a person's immune system. In addition, the status of the immune system can affect a person's susceptibility to infections. Thus, there is a continuing need in the art for methods of counteracting the effects of toxic insults such as hydrocarbons to the body, especially those which affect the immune system.

SUMMARY OF THE INVENTION

It is an object of the invention to provide a method of stimulating the immune system of an immunocompromised individual.

It is an object of the invention to provide a method of stimulating the proliferation of immune cells in a mixed cell culture.

It is another object of the invention to provide a prophylactic method for preventing a decrease in activity of an individual's immune system.

It is still another object of the invention to provide a method of stimulating maturation of an immature immune system.

It is another object of the invention to provide a method of enhancing an immune response to a viral infection.

It is yet another object of the invention to provide a method of enhancing an immune response to a bacterial infection.

It is another object of the invention to provide a method of reducing the risk of cancer development.

It is another object of the invention to provide a method for prevention of cancer metastasis.

It is still another object of the invention to provide a method for inhibiting tumor progression.

These and other objects of the invention are provided by one or more of the embodiments described below. In one embodiment of the invention a method of stimulating the immune system of an immunocompromised individual is provided. The method comprises the steps of:

administering an immune-stimulatory amount of aerosolized substance P, or a bioactive analogue thereof, to an immunocompromised individual.

According to another embodiment of the invention, a method of stimulating the proliferation of immune cells in a mixed cell culture is provided. The method comprises:

contacting a mixed cell culture with substance P, or a bioactive analogue thereof, in an amount effective to stimulate the proliferation of immune cells.

According to yet another embodiment of the invention, a prophylactic method for preventing a decrease in activity of an individual's immune system is provided. The method comprises:

administering an immune-stimulatory amount of aerosolized substance P, or a bioactive analogue thereof, to an individual at risk of a loss of activity of its immune system.

According to still another aspect of the invention, a method of stimulating the maturation of a juvenile immune system is provided. The method comprises the step of:

administering an immune-stimulatory amount of aerosolized substance P, or a bioactive analogue thereof, to juvenile individuals.

In another embodiment of the invention, a method of enhancing an immune response to a viral infection is provided. The method comprises:

administering an immune-stimulatory amount of aerosolized substance P, or a bioactive analogue thereof, to an individual infected with a virus.

In yet another embodiment of the invention a method of enhancing an immune response to a bacterial infection is provided. The method comprises:

administering an immune-stimulatory amount of aerosolized substance P, or a bioactive analogue thereof, to an individual infected with a pathogenic bacterium.

In another embodiment of the invention a method of preventing metastases in an individual having a cancer is provided. The method comprises the step of:

administering an immune-stimulatory amount of aerosolized substance P or a bioactive analog thereof, to an individual having a cancer.

In still another embodiment of the invention a method is provided for reducing the risk of cancer development in an individual. The method comprises the step of:

administering an immune-stimulatory amount of aerosolized substance P or a bioactive analog thereof, to an individual.

In yet another embodiment of the invention, a method of inhibiting tumor growth in an individual having a cancer is provided. The method comprises the step of:

administering an immune-stimulatory amount of aerosolized substance P or a bioactive analog thereof to an individual having a cancer.

These and other embodiments which are described in more detail below, provide the art with prophylactic and therapeutic means of enhancing immune responses in order to combat diseases.

DETAILED DESCRIPTION OF THE PREFERRED EMBODIMENTS

We have determined that Substance P, a neurotransmitter, also has immune system growth factor properties. This has been determined in two different model systems. In one model system, the deleterious effects of chronic JP-8 jet fuel exposure to the immune system was reversed and/or prevented by Substance P aerosol therapy. In a second system, a mouse AIDS model utilizing the LP-BM5 murine leukemia retrovirus, substance P aerosol therapy caused significant changes in the mouse spleens. In addition, Substance P aerosol therapy has been found to reduce the rate of tumor colonization and enhance survival time in tumor-challenged mammals.

The discovery of the present invention can be utilized in a number of settings. It can be used for the in vitro stimulation of immune cells in a mixed cell culture. It can be used in treating individuals who are already immunocompromised. It can be used to prevent individuals at risk of being immunocompromised, e.g., because of occupational exposure, from actually becoming immunocompromised. In addition, it can be used to accelerate maturation of a juvenile immune system. Similarly, it can be used to enhance the natural immune response to pathogens, either viral or bacterial, as well as to tumors.

Aerosolization has been found to be a very effective means of administering Substance P to mammalian subjects. However, other means, as are known in the art, such as intravenous, subcutaneous, intramuscular, intraperitoneal, and intraarterial administration can be used as alternatives. Typically these will be by injection, although other delivery means can also be used such as transdermal absorption. Any such means as is known in the art can be applied.

Substance P (RPKPQQFFGLM-NH$_2$) or any of its bioactive analogues can be used in the methods of the present invention. These include, but are not limited to: [Met-OH$^{11}$]-substance P, [Met-OMe$^{11}$]-substance P, [Nle$^{11}$]-substance P, [Pro$^9$]-substance P, [Sar$^9$]-substance P, [Tyr$^8$]-substance P, [p-Cl-Phe$^{7,8}$]-substance P, and [Sar$^9$, Met(O$_2$)$^{11}$]-substance P. The latter analogue is particularly preferred. Bioactive analogs, according to the invention are those which act as competitive inhibitors of SP by binding to the SP receptor (NK-1 receptor). Other derivatives as are known in the art and commercially available (e.g., from Sigma) can be used. In addition, substance P fragments and derivatized substance P fragments may also be used. Substitution, deletion, or insertion of one to eight amino acid residues, and preferably from one to three amino acid residues, will lead to analogs which can be routinely tested for biological activity. In addition, functional groups may be modified on SP while retaining the same peptide backbone. Again, routine testing will determine which of such modifications do not adversely affect biological activity.

Typical concentration ranges of substance P or its bioactive analogue in the aerosol administered is between 0.001 and 10 μM. Concentrations in the range of between 0.05 and 5 μM are particularly useful. In the case of administration to a mixed cell culture the substance P or its bioactive analogue need not be aerosolized. It can be advantageously administered as a liquid at a concentration between about 0.1 and 10 μM.

Among the subjects for whom aerosolized substance P therapy will be useful are those at risk of losing or those who have lost, activity of their immune systems. This may be due to advanced age, occupational exposure to hydrocarbons, immunosuppressive drugs, or immunocompromising diseases, such as AIDS or leukemia. In addition, people infected with microbial pathogens, e.g., viral or bacterial pathogens, will also benefit from a boost to their immune systems provided by aerosolized substance P. The responses of those subjects infected with rhinoviruses such as cause the common cold, and gastrointestinal bacteria, such as Salmonella species, are improved by the administration of aerosolized substance P. In addition, a boosted immune response as provided by Substance P is useful in preventing the establishment, progression, and metastases of cancers. Those at elevated risk of developing tumors, either because of occupational exposure, environmental exposure, or genetic composition, can receive the therapy of the present invention to reduce the risk of tumor formation. In addition, those who already have established cancers, will benefit from the therapy of the present invention which will inhibit the progression of tumor growth as well as inhibit the process of metastasis to other sites in the body. Tumors which are susceptible to this treatment include, but are not limited to, melanoma, breast cancer, lymphoma, lung cancer, leukemia, brain tumors, kidney tumors, liver tumors, and colorectal cancer.

Chronic hydrocarbon exposure is experienced by workers in the areas of oil refineries, oil drilling, pesticide operations, gas station attendants, engine mechanics, and plastics workers. All of these types of workers are at risk of lowered immune function due to their occupations. These workers will benefit from the treatment of the present invention.

Suitable devices for administering the aerosol of the present invention include nebulizers as well as hand-held aerosol "puffer" devices. Suitable treatment regimens for treatment according to the present invention include daily treatment by aerosol. Other modes of treatment include continual transdermal infusion, intravenous injection, subcutaneous injection, and orally. Suitable formulations of substance P for administration are any which are pharmaceutically acceptable and in which substance P retains its biological activity. Generally, such formulations are substance P dissolved in normal sterile saline.

EXAMPLES

Example 1

The effect of Substance P therapy on virally-induced immunocomprised mammals.

We have determined that Substance P, a neurotransmitter, also has immune system growth factor properties. In a mouse model utilizing the LP-BM5 murine leukemia retrovirus to simulate HIV infection, substance P aerosol therapy caused significant changes in the mouse spleens.

C57BL6 mice, average weight of 25–30 grams, were infected with the LP-BM5 murine leukemia retrovirus to simulate the human AIDS virus. One week after inoculation, substance P aerosol therapy was initiated on a Monday-Wednesday-Friday (3 days/week) basis utilizing the IN-TOX exposure chamber set-up previously described for the JP-8 jet fuel exposure study. The mice were divided into two groups; LP-BM5 virus only and LP-BM5 virus +substance P aerosol therapy at 1 $\mu$M concentration. The mice were killed at 4 and 8 weeks post-inoculation.

Mitogenesis of Spleen B and T Cells

The proliferation of splenic B and T cells induced by mitogens was determined by incorporation of radioactive thymidine. Splenocytes in 0.1 ml of cell culture medium ($1\times10^7$ cells/ml) were cultured in 96-well flat-bottom cultured plates with ConA and lipopolysaccharide, 5 micrograms/ml). The cells were incubated at 37° C., 5% $CO_2$ incubator for 72 hours for ConA-induced T cell proliferation, and then pulsed with $^3$H-thymidine (1 microCurie/well). After 4 hours for radioactive thymidine uptake, the cells were harvested by a cell sample harvester. Radioactivity was determined by a liquid scintillation counter (Tri-Carb, 2200CA). The T and B cell mitogenesis values were recorded as counts per min in $1\times10^7$ cells/ml.

Cytokine ELISA Assays

Spleen cytokine assays for interleukin-6 and interferon-gamma were conducted by standard mouse ELISA assays. The antibodies for IL-6 and interferon-gamma were purchased from Genzyme, Inc. and Collaborative Research, respectively. Briefly, flat bottom polyvinylchloride 96-well enzyme immunoassay plates were coated with 1–4 mg/ml monoclonal antibody in 0.05 ml bicarbonate buffer (pH 9.6) to each cytokine. After washing in phosphate-buffered saline containing 0.05% (v/v) Tween-20, plates were incubated in blocking reagent (1% bovine serum albumin in buffer). For the standard curves for each cytokine assay, serial dilutions of recombinant cytokine were added to a set of wells from anti-cytokine coated plates. After two hours at room temperature and three subsequent washings, biotinylated-anti-cytokine will be added to respective wells diluted 1:500 in blocking reagent. All plates were then incubated for an additional two hours at room temperature, washed three times, then 50 ml of 1:5000 avidin-peroxidase was added. After an additional 3 washes, 50 ml of the substrate mixture was added to each well (ABTS plus hydrogen peroxide solution). After an incubation at room temperature for 10–15 minutes, stopping reagent (50 ml of a 12 g NaOH in 50 ml water solution) was added. Readings were taken at 405 nm with 490 nm reference using a microELISA spectrophotometric plate reader. Values of interluekin-6 and interferon-gamma were expressed as nanograms/ml.

The data at 4 weeks after infection are the following:

| Group | 24 Hours in Culture | 48 Hours in Culture | 72 Hours in Culture |
|---|---|---|---|
| Spleen T Cell Mitogenesis | | | |
| LP-BM5 Only | 2413 (28) | 1366 (25) | 3022 (45) |
| SP + Virus | 2963 (56) | 2769 (23)* | 4362 (69)* |
| Spleen B Cell Mitogenesis | | | |
| LP-BM5 Only | 1360 (364) | 1220 (177) | 1041 (117) |
| SP + Virus | 2063 (448)* | 1369 (231) | 1642 (158)* |

| Spleen Cytokine Production (Units are nanogram/ml.) | | |
|---|---|---|
| Group | Interleukin-6 | Interferon-Gamma |
| LP-BM5 Only | 0.051 (0.009) | 0.2894 (0.048) |
| SP + Virus | 0.1334 (0.02)** | 1.5188 (0.21)** |

*p less than 0.05.
**p less than 0.01.
The number in parenthesis is the standard error of the mean.

These changes in spleen function were not accompanied by an increase in total cell numbers in the SP+Virus Group compared to the LP-BM5 group.

Additional data were collected in the mouse AIDS model utilizing the LP-BM5 murine leukemia virus to simulate the AIDS virus. The additional data were collected at 8 weeks post-infection with LP-BM5 virus.

| Spleen T Cell Mitogenesis 72 hours in culture- | |
|---|---|
| LP-BM5 Only | 1372 (233) |
| SP + Virus | 3127 (77)* |

*p = 0.02.

| Spleen B Cell Mitogenesis 72 hours in culture- | |
|---|---|
| LP-BM5 Only | 2555 (296) |

-continued

| SP + Virus | 3227 (854)* |
|---|---|

*Not significant.

Spleen Cytokine Production (Units are nanogram/ml.)

| Group | Interleukin-6 | Interferon-Gamma |
|---|---|---|
| LP-BM5 Only | 0.0617 (0.008) | 0.1503 (0.03) |
| SP + Virus | 0.1480 (0.02) | 1.072 (0.09)** |

*p = 0.02.
**p = 0.0002.

Example 2

The effect of Substance P therapy on JP-8 jet fuel exposed mice.

C57BL6 mice, average weight of 25–30 grams, were administered different JP-8 jet fuel concentrations; sham JP-8 (ambient air), 500 mg/m$^3$, or 2500 mg/m$^3$ for seven days (1 hour/day) over a total time period of nine days. The exposure regimen consisted of the aerosolization of JP-8 jet fuel by placing 5–10 mls JP-8 jet fuel in a Devilbiss nebulizer, Model #99, that produces aerosol droplets by sonication. Since mice are nose-breathers, they were exposed to the aerosol/vapor mixture via nose-only presentation while they were held in individual loading tubes. The tubes were nose-fitted to receiving adaptors that originated from the common anodized aluminum exposure chamber (volume 0.3 m$^3$, IN-TOX, Albuquerque, N.Mex.). Noses were positioned in the exposure ports to minimize systemic absorption that might occur during total body exposure or through the process of self-grooming after exposure. The mice were rotated on a daily basis through the 24-adaptor positions of the exposure chamber. This was done to minimize proximity to the jet fuel source as a variable in exposure concentration or composition. Passive entrainment of the jet fuel aerosol/vapor mix and room air through the IN-TOX chamber was conducted by vacuum (15 liters/min). The vacuum was applied to the exposure chamber on the side opposite the fuel source. Animal exposure ports not in use were sealed during the exposure period. Longitudinal controls were sham-exposed in a manner identical to those receiving jet fuel, except that only room air was introduced into the exposure chamber. The exposure chamber was thoroughly cleaned prior to the longitudinal control group's exposure.

The substance P aerosol therapy was performed at the completion of the JP-8 jet fuel exposure. The nebulizer was modified with clean hoses and a new sonication crucible. A bioactive analog of substance P, [Sar 9, Met (O$_2$)11]-substance P, in a one micromolar concentration in normal (0.85% NaCi) sterile saline was aerosolized for 15 minutes immediately following the JP-8 jet fuel exposure regimen. The substance P aerosol therapy was conducted for the same seven day period over a total time period of nine days as the JP-8 jet fuel exposure regimen.

Figure 1:
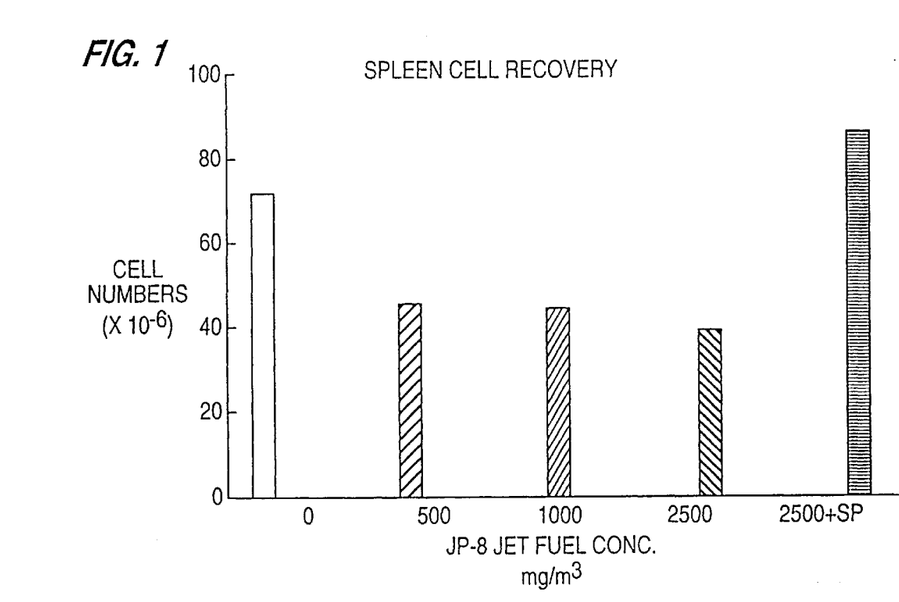
FIG. 1 shows the effect of increasing concentrations of JP-8 jet fuel on spleen cell number, as well as effect of substance P on the spleen cell number.
Figure 2:
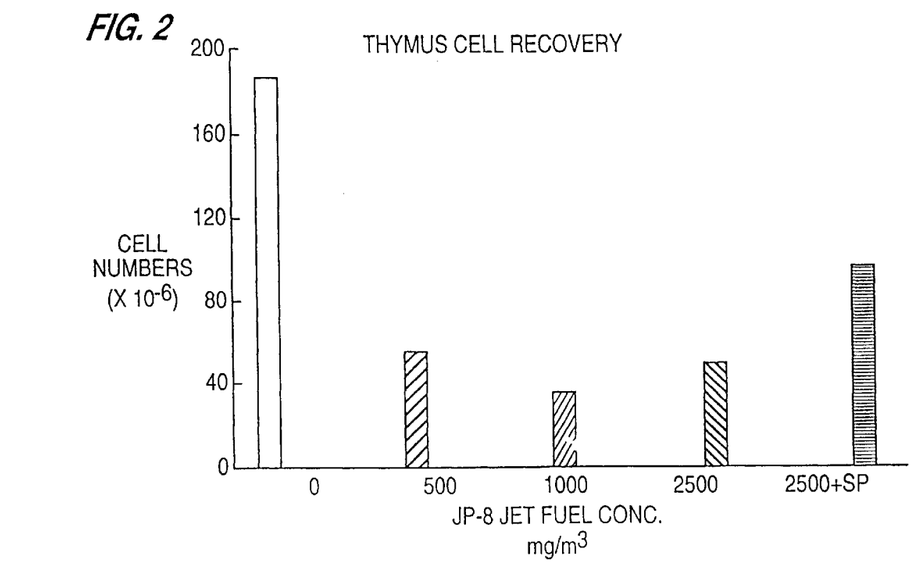
FIG. 2 shows the effect of JP-8 jet fuel and Substance P on thymus cell number.
Figure 3:
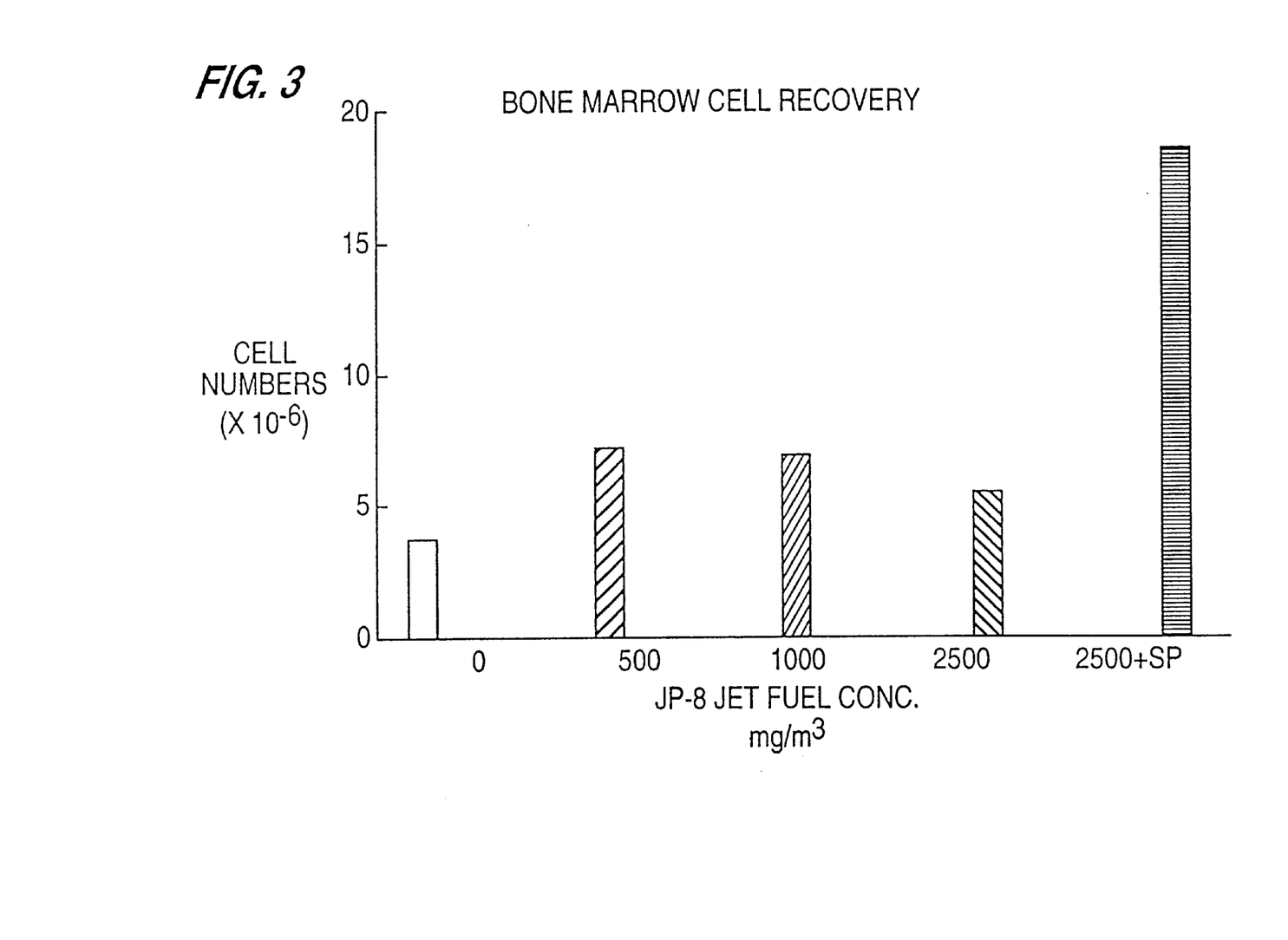
FIG. 3 shows the effect of JP-8 jet fuel and Substance P on bone marrow cells.

The results of these studies are shown in FIGS. 1, 2, and 3. FIG. 1 shows the effect of increasing concentrations of JP-8 jet fuel on spleen cell number. Also shown is the ability of substance P to totally reverse the effect of the jet fuel on the spleen cell number.

FIG. 2 shows the effect of JP-8 jet fuel on thymus cell number. Here too, Substance P substantially reverses the effect on cell number.

FIG. 3 shows the effect of JP-8 jet fuel on bone marrow cells. While JP-8 appears to stimulate the number of bone marrow cells somewhat, Substance P therapy augments the stimulation substantially.

Example 3

Immunotoxicology of exposure to jet fuel JP-8.

Inbred C57B16 mice were exposed to either 500, 1000 or 2500 mg of aerosolized JP-8 for a period of 7 days, 1 hour of exposure per day. At 24 hours after the last exposure, the animals were sacrificed and the effects of exposure on the immune system examined. Immune organs (spleen, thymus, blood, lymph nodes and bone marrow) were recovered and analyzed for effects on organ weight, total cell numbers, immune cell populations (by differentials), and lymphocyte subpopulations (by flow cytometry). Assays were also performed to examine the effects of exposure on immune function. Exposure to JP-8 was found to significantly decrease the total cell numbers in spleen and thymus of the animals, even at the lowest doses utilized. Flow cytometric analyses revealed that all lymphocyte subpopulations were affected equally, although it appeared that exposure resulted in an increase in inflammatory cells. Similar effects on immune cell subpopulations were also observed in lymph nodes. In the thymus it appeared that the immature CD4$^+$ CD8$^+$ cells were differentially lost due to exposure. In terms of immune function, JP-8 exposure resulted in a significant and profound suppression in immunological competence as assessed by mixed lymphocyte reactions to mitogens, which could not be overcome by the addition of exogenous growth factors (ie., IL-2) even at the lowest dose of exposure. An opposite effect was observed for responses to growth factor (IL2) alone, indicating that exposure may have initiated an inflammatory reaction. Interestingly, treatment of the exposed animals with Substance P invariably reversed the effects on all measured parameters of JP-8 exposure to almost normal levels. Thus, it appears that exposure of animals to even low doses of JP-8 has a significant suppressive effect on the immune system in terms of both immune cell numbers and immune cell function. However, these effects are prevented or ameliorated by treatment of the animals with Substance P.

Example 4

The mice were infected with syngeneic human melanoma B16 cancer cells by tail vein injection. The dose was 1×10$^4$ B16 tumor cells/mouse. The first group of mice (n≧4) was treated starting the next day for a total of 7 days with our standard substance P aerosol therapy of 1 μM SP for 15 min/day. The second group of mice was given their substance P aerosol therapy starting one week after the injection of the B16 cells. The aerosol therapy lasted for one week. Both groups of mice and their corresponding controls (injection with B16 cells and no substance P therapy) were killed at 4 weeks post-injection with B16 cells. The data is presented as the mean number of tumor colonies observed in both lungs.

| Substance P Therapy Starting Immediately After B16 Cells Injection | | |
|---|---|---|
| Controls | 105 | |
| Substance P | 39 | 62.9% reduction in tumors |
| Substance P Therapy Starting One Week After B16 Cells Injection | | |
| Controls | 30 | |
| Substance P | 1 | 97.0% reduction in tumors |

Example 5

The mice were infected with 1×10$^5$ human melanoma B16 cancer cells by tail vein injection. Again, the first group of mice (n≧4) was treated with our standard substance P aerosol therapy of 1 µM SP for 15 min/day for 7 days. The second group of mice was treated with the same SP dose starting at one week post-injection for seven days. Survival was assessed to determine the effect of SP aerosol therapy in prolonging life when mice are challenged with a massive cancer challenge.

| Controls - Syngeneic Murine B16 Cancer Cells and no SP |  |
|---|---|
| Days alive after B16 Cells | 25.3 (2.6) |
| SP Therapy Starting Immediately After B16 Cells |  |
| Days alive after B16 cells | 31.5 (3.8) |
| SP Therapy Starting One Week After B16 Cells |  |
| Days alive after B16 cells | 26.0 (2.0) |

Data are expressed as mean (SEM).

Example 6

Blastogenesis and Mixed lymphocyte response (MLR) assays: Blastogenesis and MLR assays are set up in 96 well microtitre plated in replicates of 6. Responder cells are plated at $1 \times 10^5$ cells/well and are stimulated as indicated (with either media, alloantigen, growth factors or mitogens). After 72 hours the plates are pulsed with 1 uCi/well of $^3$H-thymidine for 18 hours. The wells are then harvested using a Ph.D. cell harvester, the filters dried and scintillation counting performed. The data is presented as the stimulated dpm and is represented as the stimulation index (SI) (Harris et al., Proc. Natl. Acad Sci. USA 89:10006 (1992)).

Flow cytometric analyses (FACS): One- and two-color FACS analyses are performed using a Becton-Dickinson FACStar Plus flow cytometer. Cells are stained with the indicated monoclonal antibodies according to standard procedures (Harris et al., id). Cells alone and cells reacted with conjugated isotype control, irrelevant mAbs are used as controls. Data is presented as the percentage of cells staining positive for each individual mAb.

Organ Weight and Total Cell Recovery: For each of the immune system organs (spleen, lymph nodes and thymus) the wet weight is determined after removal using a microbalance. After processing of the organs into single cell suspensions the cell numbers and viabilities are determined using trypan blue staining. Histochemical differentials are performed at this time. Cell numbers and viabilities are again determined after centrifugation of the cell suspensions through density gradients to obtain mononuclear cells.

Figure 4:
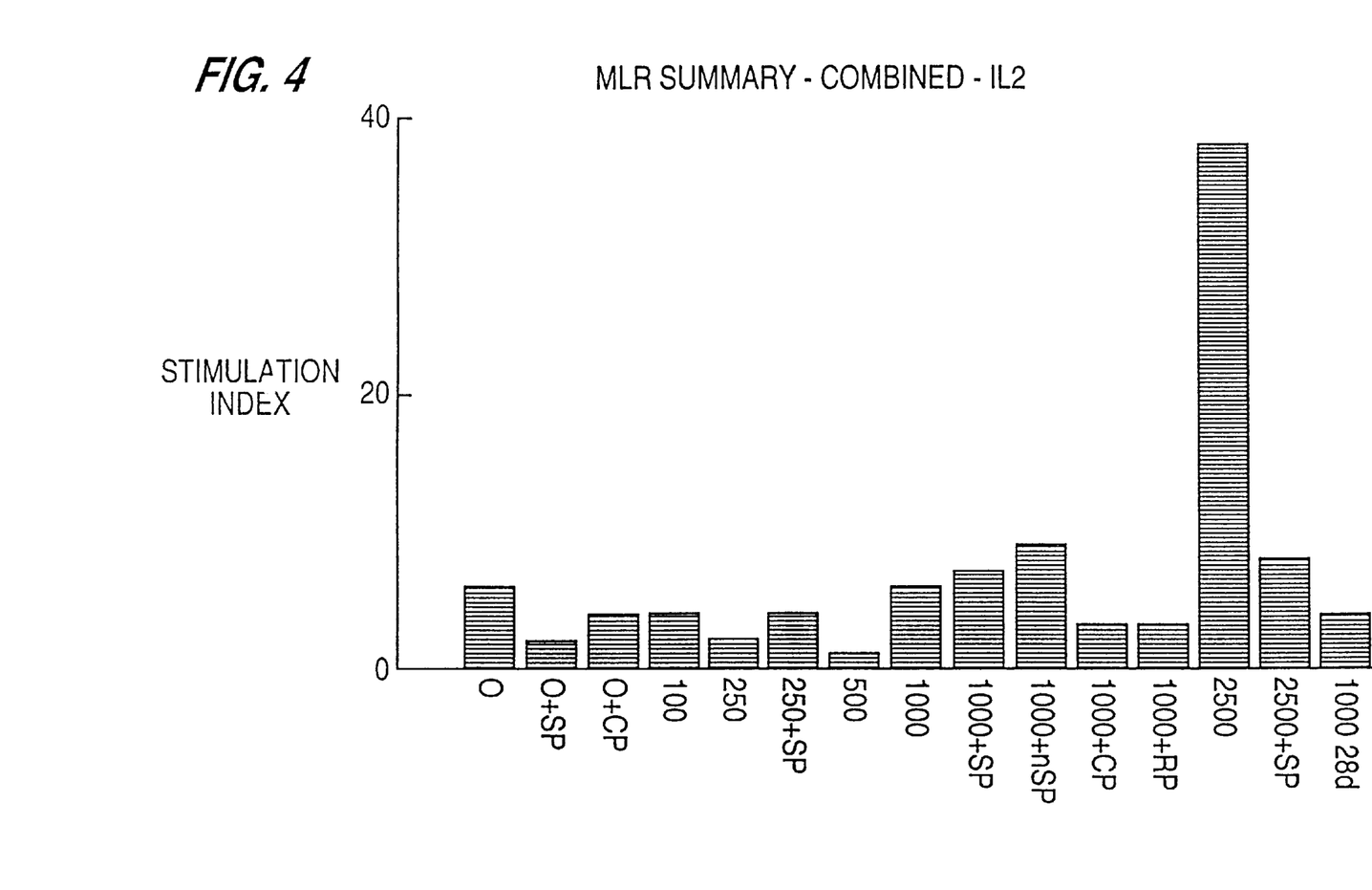
FIG. 4 shows a summary of the mixed lymphocyte response assays in the presence of $10^3$ units/ml interleukin-2. Along the x-axis the numbers represent 1 mg of substance P or antagonist for 15 min. daily for 7 days (unless indicated as 28 days). SP=substance P; CP=substance P antagonist designated CP-96,345; RP=substance P antagonist designated MRP-67,580; nSP=1 nanomolar substance P.
Figure 5:
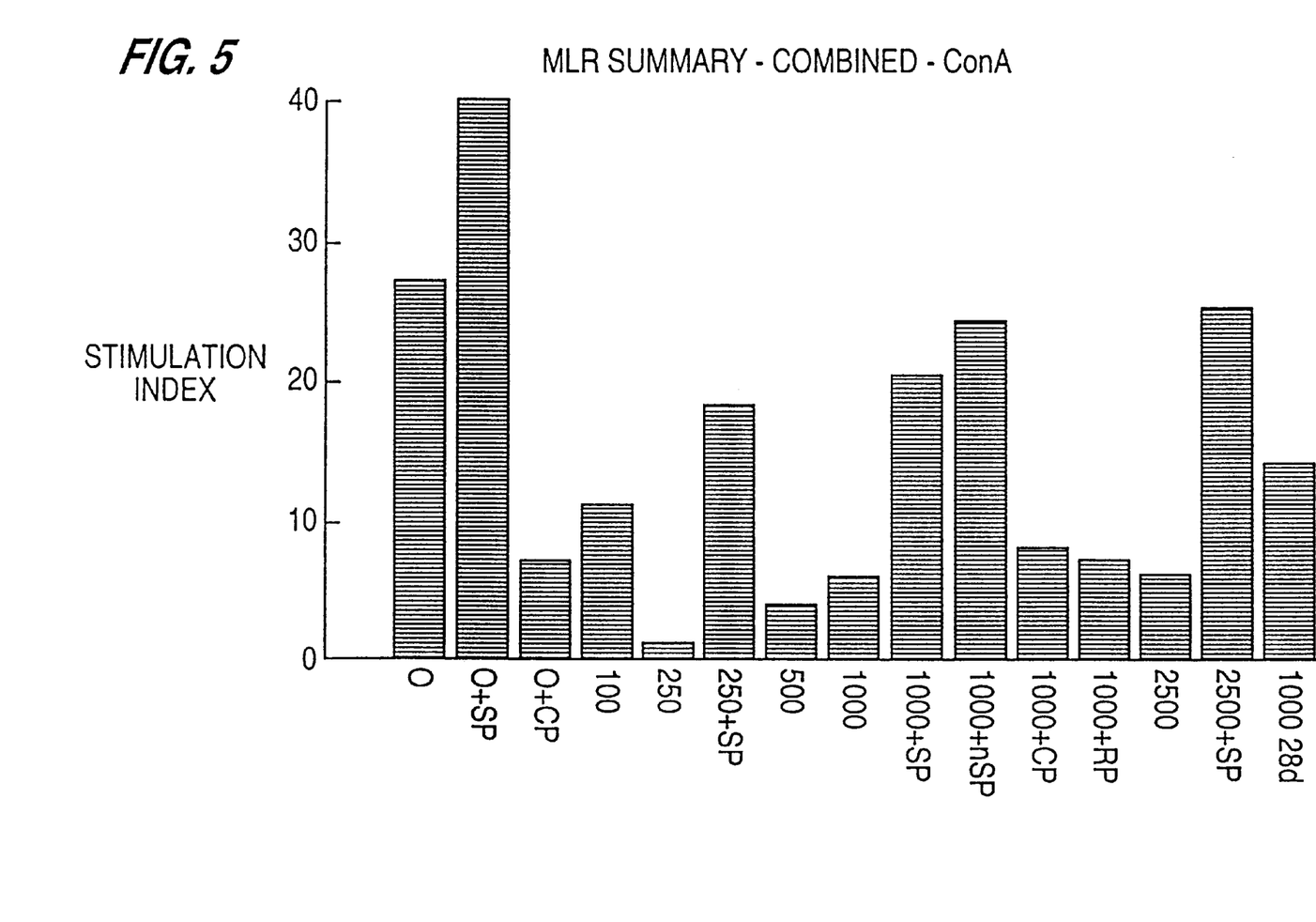
FIG. 5 shows a summary of the mixed lymphocyte response assays in the presence of 5 μg/ml conconavalinA. Along the x-axis the numbers represent 1 mg of substance P or antagonist added. SP=substance P; CP=substance P antagonist designated CP-96,345; RP=substance P antagonist designated MRP-67,580; nSP=1 nanomolar substance P.
Figure 6:
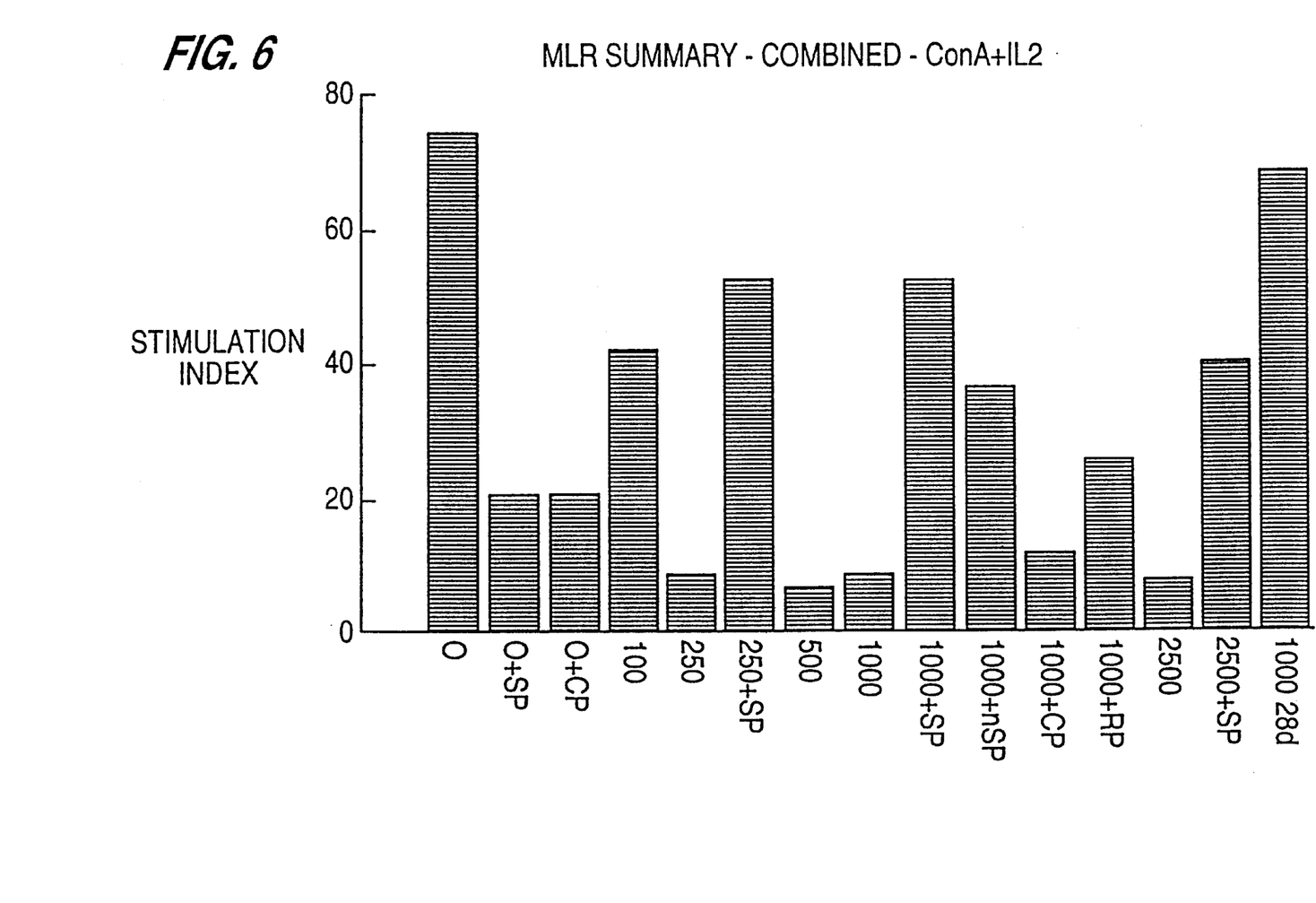
FIG. 6 shows a summary of the mixed lymphocyte response assays in the presence of combined 5 μg/ml conconavalinA and 30 units/ml interleukin-2. Along the x-axis the numbers represent 1 mg of substance P added. SP=substance P; CP=substance P antagonist CP-96,345; RP=substance P antagonist MRP-67,580; nSP=1 nanomolar substance P.

The results are summarized in FIGS. 4–6 and Tables 1 and 2.

TABLE 1

SUMMARY:
ORGAN WEIGHTS AND CELL NUMBERS: COMBINED MICE

| Dose | Organ | Weight | Cell Number | N |
|---|---|---|---|---|
| 0 | Spleen | 0.23 | 53 | 20 |
| 0 + SP |  | 0.10 | 30 | 2 |
| 0 + CP |  | 0.12 | 16 | 6 |
| 100 |  | 0.28 | 61 | 7 |
| 250 |  | 0.23 | 62 | 3 |
| 250 + SP |  | 0.16 | 40 | 6 |
| 500 |  | 0.19 | 37 | 12 |

TABLE 1-continued

SUMMARY:
ORGAN WEIGHTS AND CELL NUMBERS: COMBINED MICE

| Dose | Organ | Weight | Cell Number | N |
|---|---|---|---|---|
| 1000 |  | 0.19 | 40 | 19 |
| 1000 + SP |  | 0.14 | 72 | 13 |
| 100 + nSP |  | 0.11 | 58 | 3 |
| 1000 + CP |  | 0.16 | 7 | 9 |
| 1000 + RP |  | 0.10 | 37 | 3 |
| 2500 |  | 0.16 | 32 | 2 |
| 2500 + SP |  | 0.10 | 87 | 5 |
| 1000 − 28d |  | 0.10 | 41 | 3 |

SUMMARY:
ORGAN WEIGHTS AND CELL NUMBERS: COMBINED MICE

| Dose | Organ | Weight | Cell Number | N |
|---|---|---|---|---|
| 0 | Thymus | 0.13 | 103 | 22 |
| 0 + SP |  | 0.04 | 18 | 2 |
| 0 + CP |  | 0.12 | 50 | 6 |
| 100 |  | 0.10 | 66 | 7 |
| 250 |  | 0.14 | 32 | 3 |
| 250 + SP |  | 0.06 | 20 | 6 |
| 500 |  | 0.11 | 66 | 12 |
| 1000 |  | 0.11 | 49 | 18 |
| 1000 + SP |  | 0.11 | 78 | 13 |
| 1000 + nSP |  | 0.04 | 78 | 3 |
| 1000 + CP |  | 0.12 | 75 | 9 |
| 1000 + RP |  | 0.03 | 72 | 3 |
| 2500 |  | 0.08 | 40 | 7 |
| 2500 + SP |  | 0.08 | 96 | 5 |
| 1000 − 28d |  | 0.03 | 95 | 3 |

SUMMARY:
ORGAN WEIGHTS AND CELL NUMBERS: COMBINED MICE

| Dose | Organ | Cell Number | N |
|---|---|---|---|
| 0 | LN | 6.2 | 22 |
| 0 + SP |  | ND | 2 |
| 0 + CP |  | 9.8 | 6 |
| 100 |  | 5.6 | 7 |
| 250 |  | 3.6 | 3 |
| 250 + SP |  | 10.8 | 6 |
| 500 |  | 12.9 | 12 |
| 1000 |  | 9.3 | 19 |
| 1000 + SP |  | 5.0 | 13 |
| 1000 + nSP |  | 10.8 | 3 |
| 1000 + CP |  | 7.1 | 9 |
| 1000 + RP |  | 6.8 | 3 |
| 2500 |  | 0.8 | 7 |
| 2500 + SP |  | 5.0 | 5 |
| 1000 − 28d |  | 14.8 | 3 |

SUMMARY:
ORGAN WEIGHTS AND CELL NUMBERS: COMBINED MICE

| Dose | Organ | Cell Number | N |
|---|---|---|---|
| 0 | BM | 16 | 22 |
| 0 + SP |  | 9 | 2 |
| 0 + CP |  | 29 | 6 |
| 100 |  | 28 | 7 |
| 250 |  | 33 | 3 |
| 250 + SP |  | 23 | 6 |
| 500 |  | 12 | 12 |
| 1000 |  | 14 | 19 |

-continued

SUMMARY: ORGAN WEIGHTS AND CELL NUMBERS: COMBINED MICE

| Dose | Organ | Cell Number | N |
|---|---|---|---|
| 1000 + SP | | 21 | 13 |
| 1000 + nSP | | 31 | 3 |
| 1000 + CP | | 22 | 9 |
| 1000 + RP | | 27 | 3 |
| 2500 | | 5 | 7 |
| 2500 + SP | | 19 | 5 |
| 1000 − 28d | | 34 | 3 |

TABLE 2

SUMMARY: FACS ANALYSES: COMBINED MICE

| Dose | Organ | CD3 | CD8 | CD4 | MAC1 | CD45 | N |
|---|---|---|---|---|---|---|---|
| 0 | Spleen | 39 | 12 | 22 | 4 | 26 | 21 |
| 0 + SP | | 42 | 11 | 26 | 1 | 23 | 2 |
| 0 + CP | | 32 | 7 | 21 | 3 | 24 | 6 |
| 100 | | 46 | 6 | 31 | 3 | 18 | 6 |
| 250 | | 38 | 4 | 32 | 1 | 17 | 3 |
| 250 + SP | | 62 | 3 | 27 | 1 | 21 | 6 |
| 500 | | 36 | 12 | 23 | 4 | 24 | 12 |
| 1000 | | 32 | 8 | 17 | 8 | 24 | 18 |
| 1000 + SP | | 34 | 10 | 18 | 5 | 20 | 10 |
| 1000 + nSP | | 60 | 5 | 15 | 1 | 41 | 3 |
| 1000 + CP | | 34 | 9 | 16 | 11 | 26 | 9 |
| 1000 + RP | | 47 | 5 | 16 | 1 | 39 | 3 |
| 2500 | | 34 | 16 | 24 | 9 | ND | 7 |
| 2500 + SP | | 38 | 14 | 26 | 3 | 31 | 8 |
| 1000 − 28d | | 66 | 10 | 20 | 5 | 16 | 3 |

| | | | |
|---|---|---|---|
| 1000 + nSP | | 4 | 3 |
| 1000 + CP | | 3 | 9 |
| 1000 + RP | | 6 | 3 |
| 2500 | | 0.1 | 7 |
| 2500 + SP | | 2 | 5 |
| 1000 − 28d | | 7 | 3 |

SUMMARY: FACS ANALYSES: COMBINED MICE

| Dose | Organ | CD3 | SP4 | SP8 | DP | DN | N |
|---|---|---|---|---|---|---|---|
| 0 | Thymus | 18 | 13 | 6 | 74 | 8 | 21 |
| 0 + SP | | 10 | 6 | 2 | 84 | 7 | 2 |
| 0 + CP | | 18 | 12 | 3 | 75 | 13 | 6 |
| 100 | | 13 | 12 | 4 | 77 | 6 | 6 |
| 250 | | 11 | 17 | 2 | 77 | 4 | 3 |
| 250 + SP | | 24 | 22 | 5 | 68 | 5 | 6 |
| 500 | | 14 | 16 | 6 | 72 | 11 | 12 |
| 1000 | | 22 | 20 | 11 | 50 | 18 | 18 |
| 1000 + SP | | 20 | 16 | 6 | 65 | 10 | 10 |
| 1000 + nSP | | 25 | 16 | 7 | 69 | 7 | 3 |
| 1000 + CP | | 17 | 17 | 7 | 65 | 12 | 9 |
| 1000 + RP | | 16 | 12 | 8 | 70 | 10 | 3 |
| 2500 | | 24 | 18 | 8 | 64 | 9 | 7 |
| 2500 + SP | | 16 | 15 | 5 | 64 | 19 | 8 |
| 1000 − 28d | | 13 | 9 | 5 | 82 | 14 | 3 |

SUMMARY: FACS ANALYSES: COMBINED MICE

| Dose | Organ | CD3 | CD8 | CD4 | MAC1 | CD45 | N |
|---|---|---|---|---|---|---|---|
| 0 | LN | 94 | 49 | 38 | 4 | 8 | 21 |
| 0 + SP | | ND | ND | ND | ND | ND | 2 |
| 0 + CP | | 49 | 12 | 25 | 1 | 15 | 6 |
| 100 | | 76 | 22 | 50 | 1 | 15 | 6 |
| 250 | | 86 | 16 | 62 | 0 | 16 | 3 |
| 250 + SP | | 85 | 12 | 48 | 1 | 13 | 6 |
| 500 | | 53 | 14 | 36 | 6 | 11 | 12 |
| 1000 | | 72 | 24 | 33 | 4 | 17 | 18 |
| 1000 + SP | | 86 | 11 | 29 | 0 | 22 | 10 |
| 1000 + nSP | | 95 | 25 | 42 | 0 | 23 | 3 |
| 1000 + CP | | 95 | 23 | 35 | ND | ND | 9 |
| 1000 + RP | | 96 | 29 | 41 | 1 | 18 | 3 |
| 2500 | | 62 | 24 | 24 | ND | ND | 7 |
| 2500 + SP | | ND | ND | ND | ND | ND | 8 |
| 1000 − 28d | | 86 | 35 | 39 | 0 | 14 | 3 |

SUMMARY: FACS ANALYSES: COMBINED MICE

| Dose | Organ | CD3 | CD8 | CD4 | MAC1 | CD45 | N |
|---|---|---|---|---|---|---|---|
| 0 | BM | 11 | 4 | 3 | 36 | 30 | 21 |
| 0 + SP | | 12 | 1 | 11 | ND | 48 | 2 |
| 0 + CP | | 16 | 7 | 9 | 33 | 27 | 6 |
| 100 | | 16 | 4 | 8 | 11 | 56 | 6 |
| 250 | | 14 | 4 | 16 | 2 | 50 | 3 |
| 250 + SP | | 13 | 3 | 10 | 10 | 48 | 6 |
| 500 | | 18 | 8 | 8 | 37 | 24 | 12 |
| 1000 | | 14 | 2 | 6 | 23 | 37 | 18 |
| 1000 + SP | | 14 | 2 | 9 | 26 | 31 | 10 |
| 1000 + nSP | | 13 | 3 | 10 | 16 | 43 | 3 |
| 1000 + CP | | 14 | 3 | 7 | 26 | 41 | 9 |
| 1000 + RP | | 12 | 5 | 6 | 10 | 42 | 3 |
| 2500 | | 16 | 3 | 4 | 26 | 37 | 7 |
| 2500 + SP | | 6 | 6 | 3 | 34 | 24 | 8 |
| 1000 − 28d | | 20 | 9 | 11 | 12 | 44 | 3 |

SUMMARY: FACS ANALYSES: COMBINED MICE

| Dose | Organ | CD3 | CD8 | CD4 | MAC1 | CD45 | N |
|---|---|---|---|---|---|---|---|
| 0 | PBL | 55 | 13 | 29 | 11 | 19 | 21 |
| 0 + SP | | ND | ND | ND | ND | ND | 2 |
| 0 + CP | | 72 | 13 | 29 | 7 | 12 | 6 |
| 100 | | 75 | 9 | 24 | 3 | 17 | 6 |
| 250 | | ND | 6 | 33 | 1 | 23 | 3 |
| 250 + SP | | 59 | 6 | 15 | 1 | 16 | 6 |
| 500 | | 33 | 8 | 19 | 20 | 14 | 12 |
| 1000 | | 44 | 10 | 28 | 4 | 23 | 18 |
| 1000 + SP | | 61 | 10 | 23 | 3 | 22 | 10 |
| 1000 + nSP | | 78 | 8 | 25 | 2 | 29 | 3 |
| 1000 + CP | | 50 | 15 | 20 | 6 | 27 | 9 |
| 1000 + RP | | 71 | 10 | 18 | 9 | 38 | 3 |
| 2500 | | ND | ND | ND | ND | ND | 7 |
| 2500 + SP | | ND | ND | ND | ND | ND | 8 |
| 1000 − 28d | | 71 | 9 | 9 | 2 | 24 | 3 |

Conclusions

1. There were no significant differences in the effects of JP-8 based on gender (i.e., male versus female mice).
2. Short-term exposure of C57B16 mice to low doses of JP-8 jet fuel resulted in significant decreases in lymphoid cells recovered from the major immune system organs, at doses of 500 mg/m$^3$ and above.
3. Exposure to JP-8 jet fuel appeared to diminish all lymphoid subpopulations equally, with concomitant increases in inflammatory cells being observed.
4. Significant and profound suppression of immune function resulted from short-term, low dose exposure to JP-8 fuel, as shown by blastogenesis assays.

5. The majority of the effects of JP-8 jet fuel exposure on the immune system could be significantly reversed by exposure of the animals to Substance P, at both 1 uM and 1 nM doses.
6. Mice appear to recover somewhat from the immunotoxicological effects of JP-8 exposure after 28 days of exposure, although not completely.
7. Such changes in immunological competence have significant effects on the host's susceptibility to infectious disease, as well as future development of cancer and autoimmune disease.

Future studies with SP therapy will include the following assays:

Cytotoxic T lymphocyte (CTL) generation: C57BL6 mice are injected intraperitoneally with $10–50\times10^6$ mitomycin C-treated allogeneic tumor cells (e.g., P815) in a final volume of 0.5 ml of PBS. After 7–14 days, the mice are sacrificed and the peritoneal contents as well as the spleens are recovered (Shearer et al., Adv. Immunol 25:55 (1977)). Both cell sources are analyzed for CTL activity. The cells are centrifuged through a density gradient to obtain viable cells, and tested for cytotoxicity against the original stimulator cells (as well as third party cells) in a standard 4 hour $^{51}$Cr-release assays (Harris et al., Bone Marrow Transplant 14:545 (1994)). Data are presented as the percent specific lysis and are reduced to lytic units at the 20% lysis level for interexperimental comparisons (Harris et al., id).

Natural killer (NK) cell and lymphokine activated killer (LAK) cell activity: NK activity is tested by using freshly isolated spleen cells. A standard 4 hour $^{51}$Cr-release assay is used with YAC-1 tumor cells as the target cells (Harris et al., Vet. Immunol &Immunopathol. 38:272 (1993)). LAK cells are generated by incubation of spleen cells for 5–7 days with 1000 units/ml of IL 2, followed by testing for lytic activity against YAC-1, EL4 and P815 tumor cells (Harris etal., id).

Limit dilution analyses (LDA): LDA are set up using spleen cells to calculate frequencies of responding T cells to a particular stimuli (Harris et al., Bone Marrow Transplant 14:545 (1994)). Briefly, various dilutions of responder cells ($1\times10^3$, $1\times10^4$, $1\times10^5$ and $5\times10^5$) are plated in 96 well microtitre plates in replicates of 24 for each stimulus. Stimuli to be used will be IL 2, mitogens (PHA and LPS), and antigen. To determine PTLp (Proliferating T Lymphocyte precursors) frequencies the plates will be incubated for 3 days followed by a 72 hour pulse with $^3$H-thymidine. Thymidine incorporation (indicative of T cell stimulation and proliferation) will be determined by scintillation counting. To determine CTLp (Cytotoxic T Lymphocyte precursors) frequencies the plates will be incubated for a period of 7–10 days and the lytic activity of the wells tested by split well analysis (Harris, id) using a standard $^{51}$Cr-release assay. Data is presented as the frequency of responding cells in each of the assays for each of the stimuli.

B cell function: B cell function will be assessed by the ability to make an antisheep red blood cell (SRBC) antibody response. Spleen cells from JP-8 exposed mice will be stimulated in vitro with SRBC (i.e., $1\times10^6$ spleen cells+$2\times10^6$ SRBC per well in a 96 well microtitre plate) for a period of 5–7 days. The production of anti-SRBC antibodies is then assessed by both a typical plaque assay as well as by a modified cellular ELISA (McCarthy et al., J Immunol. 115:1322 (1975)).

Infectious disease susceptibility using the influenza model: To study the susceptibility to infectious disease the influenza mouse model will be utilized (Mumcuough et al., Bone Marrow Transplant 2(4):403 (1987)). Briefly, C57BL6 mice are nasally infected with sublethal concentrations of influenza virus diluted in PBS. The mice are followed for a period of 2–4 weeks for survival and signs of ill health. In some instances the surviving mice are rechallenged with a lethal concentration of influenza virus to analyze for protection (vaccination) from the original exposure. Lung viral titres will be determined after homogenization of whole lungs and centrifugation to obtain a cell-free supernatant (which will be frozen at $-80°$ C. until assay). Briefly, MDCK cells will be plated in 24 well plates and allowed to grow to confluence. Varying titres of the viral supernatant will be added and incubated for a period of 1 hour. The media is then removed and agar medium added. After an additional 2 days of incubation a 10% neutral red solution is added to the wells for 10 h and the plaques are enumerated (Kuwano et al., J Immunol. 140:1264 (1988)).

Autoimmunity development and progression using the MRL and NZB models: To investigate the effects of exposure on autoimmune disease the M.L.-lpr/lpr and NZB inbred strains of mice will be utilized (Schrieber et al., Autoimmunity 3(1):5 (1989), Saito etal., Microbiol & Immunol. 35(9):741 (1991)). These mice are especially prone to the development of SLE-like disease. After JP-8 exposure these mice will be followed for a period of 3–6 months for signs of autoimmune disease and survival. Autoimmune disease will be analyzed by the presence of external pathology, i.e., alopecia, skin sclerosis, ascites, and joint swelling. Sera will be analyzed for the presence of antinuclear and anti-dsDNA antibodies (Vidal et al., J. Exp. Med. 179:1429 (1994)).

We claim:

1. A method of stimulating the immune system of an immunocompromised individual, comprising the steps of:
   administering an immune-stimulatory amount of aerosolized substance P, or a bioactive analogue thereof selected from the group consisting of: [Met-OH$^{11}$]-substance P, [Met-OMe$^{11}$]-substance P, [Nle$^{11}$]-substance P, [Pro$^9$]-substance P, [Sar$^9$]-substance P, [Tyr$^8$]-substance P, [p-Cl-Phe$^{7,8}$]-substance P, and [Sar$^9$,Met (0$_2$)$^{11}$]-substance P, to an immunocompromised individual, whereby at least one immune stimulatory effect is produced in the immunocompromised individual selected from the group consisting of: (1) splenic B cells demonstrate increased proliferation in response to mitogens; (2) splenic T cells demonstrate increased proliferation in response to mitogens; (3) splenic cells produce increased interleukin-6; (4) splenic cells produce increased interferon γ; (5) spleen cell number is increased; (6) thymus cell number is increased; (7) bone marrow cell number is increased.

2. The method of claim 1 wherein a bioactive analogue is administered.

3. The method of claim 2 wherein the bioactive analogue is [Sar$^9$, Met (0$_2$)$^{11}$]-substance P.

4. The method of claim 1 wherein the immunocompromised individual has been chronically exposed to hydrocarbons.

5. The method of claim 1 wherein the immnunocompromised individual is HIV-positive.

6. The method of claim 1 wherein the immunocompromised individual has leukemia.

7. The method of claim 1 wherein the concentration substance P or the bioactive analogue in the administered aerosol is between 0.001 and 10 μM.

* * * * *